US007736858B2

(12) United States Patent
Boone et al.

(10) Patent No.: US 7,736,858 B2
(45) Date of Patent: Jun. 15, 2010

(54) METHOD FOR DISTINGUISHING ULCERATIVE COLITIS FROM CROHN'S DISEASE BY DETECTING THE PRESENCE OF FECAL ANIT-NEUTROPHIL CYTOPLASMIC ANTIBODIES (ANCA)

(75) Inventors: James Hunter Boone, Christiansburg, VA (US); David Maxwell Lyerly, Radford, VA (US); Tracy Dale Wilkins, Riner, VA (US)

(73) Assignee: Techlab, Inc., Blacksburg, VA (US)

( * ) Notice: Subject to any disclaimer, the term of this patent is extended or adjusted under 35 U.S.C. 154(b) by 0 days.

(21) Appl. No.: 10/656,034

(22) Filed: Sep. 5, 2003

(65) Prior Publication Data
US 2004/0126898 A1 Jul. 1, 2004

Related U.S. Application Data

(60) Provisional application No. 60/408,809, filed on Sep. 5, 2002.

(51) Int. Cl.
*G01N 33/53* (2006.01)
(52) U.S. Cl. ...................................................... 435/7.1
(58) Field of Classification Search ......... 436/506–508, 436/63, 177, 179, 811; 435/7.24, 965
See application file for complete search history.

(56) References Cited

U.S. PATENT DOCUMENTS

| 5,359,038 | A | | 10/1994 | Padron |
| 5,552,292 | A | | 9/1996 | Uchida et al. |
| 5,681,699 | A | | 10/1997 | Rotter et al. |
| 5,691,151 | A | * | 11/1997 | Braun et al. ............... 435/7.2 |
| 5,750,355 | A | | 5/1998 | Targan et al. |
| 5,874,233 | A | * | 2/1999 | Targan et al. .............. 435/7.24 |
| 5,916,748 | A | * | 6/1999 | Targan et al. ................. 435/6 |
| 5,932,429 | A | | 8/1999 | Targan et al. |
| 5,968,741 | A | | 10/1999 | Plevy et al. |
| 6,008,335 | A | | 12/1999 | Rotter et al. |
| 6,074,835 | A | * | 6/2000 | Braun et al. ............... 435/7.21 |
| 6,218,129 | B1 | | 4/2001 | Walsh et al. |
| 6,537,768 | B1 | * | 3/2003 | Braun et al. ............... 435/7.32 |
| 6,667,160 | B2 | * | 12/2003 | Fine ......................... 435/7.92 |
| 6,818,181 | B2 | * | 11/2004 | Lee ............................. 422/61 |
| 6,872,540 | B2 | * | 3/2005 | Boone et al. ................. 435/7.1 |
| 6,884,625 | B2 | * | 4/2005 | Lee ............................ 436/164 |
| 2002/0169286 | A1 | * | 11/2002 | Middeldorp et al. ........ 530/350 |
| 2004/0126898 | A1 | | 7/2004 | Boone et al. |
| 2004/0137536 | A1 | | 7/2004 | Boone |

FOREIGN PATENT DOCUMENTS

| EP | 0615129 A2 | 9/1994 |
| WO | WO 97/39356 | 10/1997 |
| WO | WO 98/46997 | 10/1998 |
| WO | 9960403 A1 | 11/1999 |
| WO | WO 99/60403 | 11/1999 |
| WO | WO 01/11334 A2 | 2/2001 |
| WO | WO2004022713 | 3/2004 |
| WO | WO2004037073 | 5/2004 |

OTHER PUBLICATIONS

Picarelli, A. et al. Antiendomysial antibody detection in fecdal supernatants: In vivo proof that small bowel mucosa is the site of antiendomysial antibody production. Am. J. Gastroenterol. 2002;97:95-98.*
Sanders, D.S. et al. Association of adult coeliac disease with irritable bowel syndrome: a case-control study in patients fulfilling ROME II criteria referred to secondary care. LANCET 2001;358:1504-1508.*
Inflammatory Bowel Diseases, MeSH Database, National Library of Medicine & National Institutes of Health, available at http://www.ncbi.nlm.gov. 2 pages total.*
Functional Colonic Diseases, MeSH Database, National Library of Medicine & National Institutes of Health, available at http://www.ncbi.nlm.gov. 1 page total.*
Mayet, W.J. et al. The pathophysiology of anti-neutrophil cytoplasmic antibodies (ANCA) and their clinical relevance. CRIT. REV. ONCOL. HEMATOL. 1996;23:151-165.*
Esaguy, N. et al. Mycobacteria and human autoimmune disease: direct evidence of cross-reactivity between human lactoferrin and the 65-kilodalton protein of tubercle and leprosy bacilli. Infection & Immunity. 1991;59:1117-1125.*
Armitage & Colton, Random Sample, Encyclopedia of Biostatistics, John Wiley & Sons (1998), vol. 5, p. 3686.*
Armitage & Colton, Selection BIAS, Encyclopedia of Biostatistics, John Wiley & Sons (1998), vol. 5, p. 4045.*
Armitage & Colton, Sampling Distribution, Encyclopedia of Biostatistics, John Wiley & Sons (1998), vol. 5, pp. 3933-3935.*
Armitage & Colton, Sampling Frames, Encyclopedia of Biostatistics, John Wiley & Sons (1998), vol. 5, pp. 3935-3939.*
Ferguson, A. et al. Technical report: results of immunological tests on faecal extracts are likely to be extremely misleading. Clin. Exp. Immunol. 1995;99:70-75.*
O'Mahony, S. et al. Appraisal of gut lavage in the study of intestinal humoral immunity. GUT. 1990;31:1341-1344.*

(Continued)

*Primary Examiner*—Jacob Cheu
(74) *Attorney, Agent, or Firm*—Shook, Hardy & Bacon L.L.P.

(57) ABSTRACT

A method and apparatus for the differentiation of ulcerative colitis from Crohn's disease and other gastrointestinal illnesses using the presence of anti-neutrophil cytoplasmic antibodies (ANCA) as a marker of ulcerative colitis is described. The apparatus consists of either a qualitative enzyme-linked immunoassay or other immunoassay that utilizes antibodies specific to human immunoglobulins for the measurement of total endogenous ANCA in a human sample. The method and apparatus can be used by healthcare providers to distinguish ulcerative colitis from Crohn's disease and other gastrointestinal illnesses.

8 Claims, 1 Drawing Sheet

OTHER PUBLICATIONS

Figure 1:
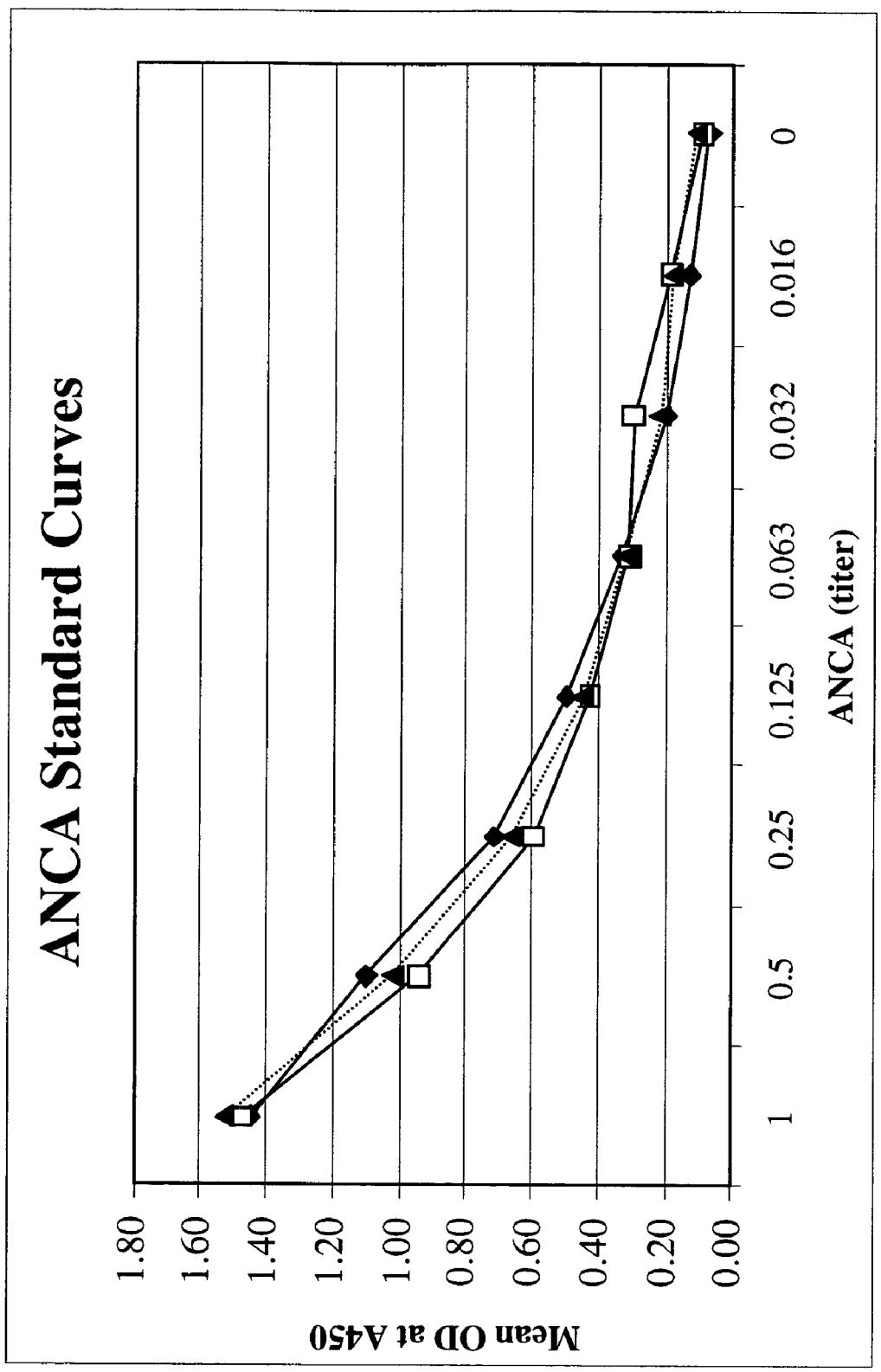

R. Barnes, S. Allan, C. Taylor-Robinson, R. Finn, P. Johnson, "Serum Antibodies Reactive with *Saccharomyces cerevisiae* in Inflammatory Bowel Disease: Is IgA Antibody a Marker for Crohn's Disease?" *Int Arch Allergy Appl Immunol* (1990) 92, 9-15.

C. Faille, D. Mackenzie, J. Michalski, and D. Poulain, "Evaluation of an Enzyme Immunoassay Using Neoglycolipids Constructed from *Candida albicans* Oligomannosides to Define the Specificity of Anti-Mannan Antibodies" *Eur. J. Clin. Microbiol. Infect. Dis.*, May 1992, 438-446.

M. Giaffer and C. Holdsworth, "Antibodies to *Saccharomyces cerevisiae* in patients with Crohn's disease and their possible pathogenic importance" *Gut* (1992) 33, 1071-1075.

S. Hanauer, "Inflammatory Bowel Disease" *The New England Journal of Medicine* (1996) 334, 841-848.

S. Hanauer and G. D'Haens, "Medical Management of Ulcerative Colitis" in Targan and Shanahan Inflammatory Bowel Disease: From Bench to Bedside, *Williams and Wilkens* (1994) 545-561.

C. Jongeneel, L. Briant, I. Udalova, A. Sevin, S. Nedospasov, and A. Thomsen, "Extensive genetic polymorphism in the human tumor necrosis factor region and relation to extended HLA haplotypes" *Proc. Natl. Acad. Sci. USA* (1991) 88, 9717-9721.

E. Lindberg, K. Magnusson, C. Tysk, and G. Jarnerot, "Antibody (IgG, IgA, and IgM) to baker's yeast *Saccharomyces cerevisiae*), yeast mannan, gliadin, ovalbumin and betalactoglobulin in monozygotic twins with inflammatory bowel disease" *Gut* (1991) 909-913.

J. Main, H. McKenzie, G. Yeaman, M. Kerr, D. Robson, C. Pennington, and D. Parratt, "Antibody to Saccharomyces cerevisiae (bakers' yeast) in Crohn's disease" *BMJ* (1988) 297 1105-1106.

H. McKenzie, J. Main, C. Pennington, and D. Parratt, "Antibody to selected strains of *Saccharomyces cerevisiae* (baker's and brewer's yeast) and *Candida albicans* in Crohn's disease" *Gut* (1990) 31, 537-538.

H. McKenzie, D. Parratt, J. Main, and C. Pennington, "Antigenic heterogeneity of strains of *Saccharomyces cerevisiae* and *Candida albicans* recognized by serum antibodies from patients with Crohn's disease" *FEMS Microbiology Immunology* (1992) 89, 219-224.

H. Yang, J. Rotter, H. Toyoda, C. Landers, D. Tyan, C. McElree, and S. Targan, "Ulcerative Colitis: A Genetically Heterogeneous Disorder Defined by Genetic (HLA Class II) and Subclinical (Antineutrophil Cytoplasmic Antibodies) Markers" *The American Society for Clinical Investigation, Inc.* (1993) 92, 1080-1084.

C. Young, A. Sonnenberg, and E. Burns, "Lymphocyte Proliferation Response to Baker's Yeast in Crohn's Disease" *Digestion* (1994) 55, 40-43.

M. Giaffer, A. Clark, C. Holdsworth, "Antibodies against *Saccharomyces Cerevisiae* (Baker's & Brewer's yeast) in Crohn's Disease" *Gastorenterology* (1991) 100, No. 5, Part 2.

G. Barclay, H. McKenzie, J. Pennington, D. Parratt, and C. Pennington, "The Effect of Dietary Yeast on the Activity of Stable Chronic Crohn's Disease" *Scand J Gastroenterol* (1992) 27, 196-200.

M. Broker, H. Harthus, and R. Barnes, "A murine monoclonal antibody directed against a yeast cell wall glycoprotein antigen of the yeast genus *Saccharomyces*" FEMS Microbiology Letters (1994) 118, 297-304.

C. Darroch, S. Christmas, and R. Barnes, "In vitro human lymphocyte proliferative responses to a glycoprotein of the yeast *Saccharomyces cerevisiae*" *Immunology Letters* (1994) 81, 247-252.

B. Heelan, S. Allan, and R. Barnes, "Identification of a 200-kDa glycoprotein antigen of *Saccharomyces cerevisiae*" *Immunology Letters* (1991) 28, 181-186.

C. Galperin and M. Gershwin, Immunopathogenesis of Gastrointestinal and Hepatobiliary Diseases, *JAMA*, (1997) 278, 1946-1955.

R. Barnes, S. Allan, C. Robinson, R. Finn, and P. Johnson, "Serum Antibodies Reactive with *Saccharomyces cerevisiae* in Inflammatory Bowel Disease: Is IgA Antibody a Marker for Crohn's Disease? " *Int. Arch. Allergy Appl. Immuno* (1990) 92, 9-15.

J. Colombel, B. Sendid, J. Quinton, P. Jacquinot, O. Goulet, A. Cortot, D. Poulain, "Anti-*Saccharomyces cerevisiae* Antibodies: A New Subclinical Marker for Crohn's Disease" *Gastroenterology* (1996) 110, No. 4.

N. Oshitani, et al., *IgG subclasses of anti Saccharomyces cerevisiae antibody in inflammatory bowel disease*; Blackwell Science Ltd., European Journal of Clinical Investigation, vol. 31, pp. 221-225,2001.

Database CAPLUS on STN, AN 2003:463137. Kane et al. 'Fecal Lactoferrin is a sensitive and specific marker in identifying intestinal inflammation' American J. Gastroenterology, 2003, vol. 98, No. 6, p. 1309-1314. See Abstract, particularly the high specificity of the neutrophil marker in detecting patients, Abstract Only.

Database CSA on STN, AN 96:19272. Martins et al. 'Correlation of lactroferrin with neutrophilic inflammation in body fluids'. Clin. Diagn. Lab Immunol. 1995, vol. 2, No. 6, p. 763-765. See abstract, Abstract Only.

U.S. Appl. No. 10/693,377, filed Oct. 24, 2003; USPTO Action Mailed: Sep. 5, 2006.

U.S. Appl. No. 10/693,377, filed Oct. 24, 2003; USPTO Office Action Mailed: Feb. 22, 2007.

U.S. Appl. No. 10/693,377, filed Oct. 24, 2003; USPTO Office Action Mailed: Sep. 25, 2007.

U.S. Appl. No. 10/693,377, filed Oct. 24, 2003; USPTO Office Action Mailed: Nov. 1, 2007.

Roozendaal, C., et al.: "Are Anti-Neutrophil Cytoplasmic Antibodies (ANCA) Clinically Useful in Inflammatory Bowel Disease (IBD)?" Clinical and Experimental Immunology, Oxford, GB, vol. 116, No. 2, May 1999.

Database Biosis [Online] Biosciences Information Service, Philadelphia, PA; 2002, Lecis Pierenrico, et al.: "[p-ANCA and ASCA Antibodies and the Differential Diagnosis Between Ulcerative Colitis and Crohn's Disease.]"; Recenti Progress In Medicina, vol. 93, No. 5, 2002.

USPTO Final Office Action mailed May 21, 2009 for U.S. Appl. No. 10/693,377, filed Oct. 24, 2003.

USPTO Nonfinal Office Action mailed Jul. 15, 2008 for U.S. Appl. No. 10/693,377, filed Oct. 24, 2003.

Bartunkova, J et al, Clinical Immunology, vol. 102(2) February, pp. 162-168, Antineutrophil Cytoplasmic antibodies, Anti-Saccharomyces cervisiae antibodies and Specific IgE to Food Allergens in Children with Inflammatory Bowel Diseases, 2002.

Halme, L et al, Scand. J. Gastroenterol. Jun. 2002, vol. 37(6), pp. 692-698, Familial and sporadic inflammatory bowel disease: comparison of clinical features and serological markers in a genetically homogeneous population.

Khan, K et al, Inflammatory Bowel Disease, pp. 325-329, vol. 8(5), 2002, Role of Serology and Routine Laboratory Tests in Childhood Inflammatory Bowel Disease.

Kossa, K et al, Eur. J. Gastroenterogyl. Hepatol, Aug. 1995, vol. 7(8), pp. 783-789, Anigen specificity of circulating antineutrophil cytoplasmic antibodies in inflammatory bowel disease.

Koutroubakis, loannis E et al, The American Journal of Gastroenterology, vol. 96(2), 2001, pp. 449-454, Anti-Saccharomyces cerevisiae Mannan Antibodies and Antineutrophil Cytoplasmic autoantibodies in Greek Patients with Inflammatory Bowel Disease.

Peen et al. Anti-lactoferrein antibodies and other types pf ANCA in ulcerative colitis, primary sclerosing cholangitis, and Crohn;s disease. Gut, 1993, 34, 56-62.

Pool et al. "Serum antineutrophil cytoplasmic autoantibodies in inflammatory bowel disease . . . " Gut, 1993, 46-50.

Quinton, Jr et al, Gut, 1998, vol. 42, pp. 788-791, Anti-Saccharomyces cerevisiae mannan antibodies combined with antineutrophil cytoplasmic autoantibodies in inflammatory bowel disease prevalence and diagnostic role.

Ruemmele, Frank M. et al, Gastroenterology, 1998, vol. 115, pp. 822-829, Diagnostic accuracy of serological assays in Pediatric inflammatory Bowel Disease.

Targan. Stephan R. et al, The Journal of Immunology, 1995. vol. 1565, pp. 3262-3267, Perinudear antl-neutrophll cytoplasmic antibodies are spontaneously produced by mucoul B cells of Ulcerative Colitis Patients.

Hoffenberg, Edward J et al, Serologic testing for inflammatory bowel disease, pp. 447-452, Apr. 1999, Journal of Pediatrics, V vol. 134.

Nakamura, RM et al, MLO Med. Lab. Obs. 2001, November, vol. 33(11) pp.-8-15, quiz pp. 6-19.

Nielsen, Ole H et al, The American Journal of Gastrosnterology, vol. 95(2), 2000, pp. 359-367, Established and Emerging Biological ActMly Markers of Inflammatory BowelDisease.

USPTO Office Action mailed Dec. 23, 2009 for U.S. Appl. No. 10/693,377, filed Oct. 24, 2003.

* cited by examiner

METHOD FOR DISTINGUISHING ULCERATIVE COLITIS FROM CROHN'S DISEASE BY DETECTING THE PRESENCE OF FECAL ANIT-NEUTROPHIL CYTOPLASMIC ANTIBODIES (ANCA)

CROSS-REFERENCE TO RELATED APPLICATIONS

This application claims the benefit of priority to U.S. Provisional Application No. 60/408,809, filed Sep. 5, 2002.

STATEMENT REGARDING FEDERALLY SPONSORED RESEARCH OR DEVELOPMENT

Not applicable.

BACKGROUND OF THE INVENTION

This invention relates to non-invasive methods for differentiating clinical subtypes of Inflammatory Bowel Disease, namely Crohn's disease (CD) and ulcerative colitis (UC). More specifically, this invention relates to a method and apparatus for aiding in the differentiation of Crohn's disease from ulcerative colitis by determining the presence of anti-neutrophil cytoplasmic antibodies (ANCA), wherein the presence of ANCA is indicative of ulcerative colitis. In addition, the presence of fecal ANCA may be used to differentiate ulcerative colitis from other gastrointestinal illnesses such as Irritable Bowel Syndrome.

An estimated 1 million Americans suffer from Inflammatory Bowel Disease (IBD). IBD is characterized by a chronic inflammatory response that results in histologic damage to the intestinal lining. Crohn's disease may involve the entire gastrointestinal tract and include inflammation extending into the transmural mucosa, whereas ulcerative colitis affects solely the large bowel and includes inflammation of the innermost lining. These two distinct diseases require a rapid differential diagnosis for optimal treatment. Conventional methods utilizing multiple endoscopy examinations and histological analysis may take years to confirm a diagnosis. U.S. Pat. No. 6,218,129 discloses a method of determining the presence of serum ANCA as a marker to diagnose IBD. However, it does not disclose a method for diagnosing ulcerative colitis in a patient diagnosed with IBD. Further, the method does not disclose testing human feces for the presence of ANCA.

Accordingly, there remains a need in the diagnostic industry for a non-invasive method of differentially diagnosing ulcerative colitis from Crohn's disease or other gastrointestinal illnesses.

SUMMARY OF THE INVENTION

Accordingly, in one of its aspects, the present invention provides non-invasive methods for differentiating between diagnoses of ulcerative colitis and Crohn's disease.

In another of its aspects, the present invention provides methods for differentiating between ulcerative colitis and Crohn's disease wherein the presence of fecal ANCA is used as a marker for ulcerative colitis.

In a further aspect, the present invention provides immunoassays, e.g., and enzyme-linked immunoassays, that utilize antibodies specific to human immunoglobulins for the measurement of total endogenous ANCA in human feces.

In yet another of its aspects, the present invention provides methods differentially diagnosing ulcerative colitis from other gastrointestinal illnesses such as Irritable Bowel Syndrome (IBS). In still another of its aspects, the present invention provides methods for diagnosing ulcerative colitis wherein the presence of ANCA is used as a marker for ulcerative colitis.

According to the present invention, the foregoing and other aspects are achieved by a non-invasive method for aiding in the differentiation of ulcerative colitis from Crohn's disease in a patient presenting with IBD. In the method of the present invention, fecal ANCA are used as a marker and the presence of ANCA indicates a differential diagnosis of ulcerative colitis. This rapid diagnosis may then be used by healthcare professionals to prescribe proper treatment.

Aspects of the present invention are further achieved by immunoassays that utilize antibodies specific to human immunoglobulins for the measurement of total endogenous ANCA in human feces.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentality's and combinations particularly pointed out in the appended claims.

BRIEF DESCRIPTION OF THE VIEW OF THE DRAWING

FIG. 1 is a graphical representation of a standard curve of anti-neutrophil cytoplasmic antibodies in accordance with an embodiment of the present invention.

DETAILED DESCRIPTION OF THE INVENTION

The present invention is directed to non-invasive methods for differentiating between ulcerative colitis and Crohn's disease using the presence of fecal ANCA as an indicator of ulcerative colitis. The present invention also is directed to a method for differentiating between ulcerative colitis and other gastrointestinal illnesses such as IBS. The present invention is further directed to immunoassays that utilize antibodies specific to human immunoglobulins for the measurement of total endogenous ANCA in human feces. The particular embodiments described herein are intended in all respects to be illustrative rather than restrictive. Alternative embodiments will become apparent to those skilled in the art to which the present invention pertains without departing from its scope.

ANCA specific immunoassays may be used to differentiate ulcerative colitis and indeterminate colitis from Crohn's disease by measurement of the presence of total endogenous ANCA. In addition to fecal matter, a sample of whole blood, serum, plasma or other bodily fluid or tissue may be tested for ANCA to diagnose ulcerative colitis. This differential diagnosis may then be used by healthcare professionals for determining optimal treatment. A qualitative immunoassay, such as a lateral flow dipstick that utilizes both monoclonal and polyclonal antibodies to endogenous human ANCA to indicate the presence of ulcerative colitis. Claim 14

In the qualitative immunoassay, the fecal or bodily sample is diluted 10 fold and added to a well containing immobilized neutrophilic cytoplasmic antigens, thus contacting the sample with neutrophilic cytoplasmic antigens to create a treated sample. If endogenous fecal ANCA is present, it will bind to the neutrophilic cytoplasmic antigens during an incubation step at 37° C. Following the incubation, polyvalent antibodies to human immunoglobulin coupled to an enzyme, such as a horseradish peroxidase enzyme, (conjugate) is added and allowed to bind to captured ANCA, thus contacting the treated sample with polyvalent antibodies to human immunoglobulin to create a readable sample. Unbound conjugate is then washed from the well and one component substrate (e.g., tetramethylbenzidene and hydrogen peroxide) is added for color development. Following the substrate incubation, 0.1M sulfuric acid is added to stop the reaction and the optical density (OD) is obtained spectrophotometrically at 450 nm.

In a clinical study, a total of 98 IBD patients were enrolled and comprised 51% males and 49% females with an age range of 0 to 69 years. The approximate 1 to 1 ratio is similar to the ratio observed in IBD patient populations. The IBS patient group had an age range of 5 to 39 years with 57% males and 43% females. The healthy controls were 55% male and 45% female and comprised the age range of 20 to 79 years. Individual numbers for each age group are shown in Table 1.

TABLE 1

Summary of patient population.

| Summary of Clinical Histories (N = 116) | Total Subjects |
|---|---|
| Total number of IBD patients | 98 |
| No. Males | 50 |
| No. Females | 48 |
| Total number of patients with Crohn's Disease | 47 |
| No. Males | 26 |
| No. Females | 21 |
| Total number of patients with ulcerative colitis | 51 |
| No. Males | 24 |
| No. Females | 27 |
| Total number of patients with irritable bowel syndrome | 7 |
| No. Males | 4 |
| No. Females | 3 |
| Total number of healthy persons | 11 |
| No. Males | 6 |
| No. Females | 5 |

There were 51 ulcerative colitis (UC) patients, 47 Crohn's disease (CD) patients, 7 irritable bowel patients (IBS), and 11 healthy (H) adults recruited for the study. Fecal specimens were collected from each enrolled patient and stored at −70° C. until tested. Specimen consistency ranged from solid to liquid. The level of fecal ANCA was determined using the qualitative ANCA ELISA as previously described. Disease activity was defined using elevated fecal lactoferrin as an indicator of intestinal inflammation. A dilution of 1:10 was used in the qualitative ELISA test and results were reported as positive (absorbance values >0.140) or negative (absorbance values <0.140). The mean optical densities, standard deviation and P values (two-tailed student T-test with unequal variance) were determined for the ANCA positive ulcerative colitis patients. Of the 26 patients that tested positive for fecal ANCA, there were four patients had Crohn's Disease, 21 had ulcerative colitis and one patient was healthy. ANCA-positive ulcerative colitis showed a mean±SD $OD_{450}$ of 0.311±0.166. The mean optical density for the ulcerative colitis patients was significantly different from IBS and healthy persons (p value<0.0005). A summary of the statistical analysis is listed in Table 2.

TABLE 2

Summary of the mean, standard deviation and P values for qualitative ELSA test Optical Densities

| Group ID | Number | Mean Optical Density | Standard Deviation | Optical Density Range | P values |
|---|---|---|---|---|---|
| ANCA + UC | 21 | 0.311 | 0.166 | 0.141-0.804 | UC vs CD p < 0.5 |
| ANCA + CD | 4 | 0.209 | 0.115 | 0.141-0.381 | UC vs CD, IBS, H p < 0.0005 |
| IBS | 7 | 0.078 | 0.027 | 0.047-0.121 | UC vs CD, IBS p < 0.005 |
| Healthy | 11 | 0.071 | 0.041 | 0.039-0.104 | UC vs IBS, H p < 0.0005 |

In the group of patients with IBD, there were 47 with Crohn's disease and 51 with ulcerative colitis. In the ulcerative colitis group, 41% were positive. In the Crohn's disease group, a total of 9% patients were positive using the qualitative ELISA test. Of the 11 healthy persons, 1 was positive and all 7 IBS patients were negative by the qualitative ELISA test. A summary of positive results for the qualitative ELISA test are shown in Table 3 and individual results are listed in Table 4 and Table 5.

TABLE 3

Summary of positive results for Crohn's disease, ulcerative colitis, and IBS

| Total Assessments N = 116 | Total | Fecal ANCA Positive | Fecal ANCA Negative |
|---|---|---|---|
| Total IBD (Crohn's disease and ulcerative colitis) | 98 | 26% (25) | 75% (73) |
| Total Crohn's Disease | 47 | 9% (4) | 91% (43) |
| Total Ulcerative Colitis | 51 | 41% (21) | 59% (30) |
| Total IBS | 7 | 0 | 7 |
| Total Healthy Persons | 11 | 9% (1) | 91% (10) |

When distinguishing ulcerative colitis from Crohn's disease, the qualitative ELISA test exhibited a sensitivity of 41% and specificity of 92%. The predictive positive and negative values were 84% and 59%, respectively, and the correlation was 65% (Table 4).

TABLE 4

Statistical evaluation using the qualitative ELISA test to distinguish Crohn's disease from ulcerative colitis

| N = 98 | Ulcerative colitis | Crohn's disease |
|---|---|---|
| ANCA positive | 21 | 4 |
| ANCA negative | 30 | 43 |
| Sensitivity | | 41% |
| Specificity | | 92% |
| Predictive Positive Value | | 84% |
| Predictive Negative Value | | 59% |
| Correlation | | 65% |

When distinguishing ulcerative colitis from irritable bowel syndrome and healthy persons, the qualitative ELISA test exhibited a sensitivity of 41% and a specificity of 92%. The predictive positive and negative values were 81% and 67%, respectively, and the correlation was 70% as shown in Table 5.

TABLE 5

Statistical evaluation using the qualitative ELISA test to distinguish ulcerative colitis from Crohn's disease, irritable bowel syndrome and healthy persons

| N = 116 | Ulcerative colitis | Crohn's disease IBS/Healthy |
|---|---|---|
| ANCA positive | 21 | 5 |
| ANCA negative | 30 | 60 |
| Sensitivity | | 41% |
| Specificity | | 92% |
| Predictive Positive Value | | 81% |
| Predictive Negative Value | | 67% |
| Correlation | | 70% |

The sensitivity of the qualitative ELISA test was determined using serial two fold dilutions of human ANCA positive serum. For the analysis, standard curves were generated using the sample diluent. The test was consistently positive to a titer of 0.063 as determined by a cutoff absorbance value of $\geq 0.200$. Individual results are shown below in Table 6 and standard curves are shown in FIG. 1.

TABLE 6

Standard curves generated using qualitative ELISA test (cut-offs are in bold)

| Human ANCA Serum | Test 1 | Test 2 | Test 3 | Mean | Std Dev |
|---|---|---|---|---|---|
| 1.000 (Neat) | 1.441 | 1.469 | 1.525 | 1.478 | 0.043 |
| 0.500 | 1.098 | 0.941 | 1.014 | 1.018 | 0.079 |
| 0.250 | 0.717 | 0.595 | 0.666 | 0.659 | 0.061 |
| 0.125 | 0.492 | 0.428 | 0.444 | 0.455 | 0.033 |
| 0.063 | 0.327 | 0.303 | 0.320 | 0.317 | 0.012 |
| 0.032 | 0.196 | 0.295 | 0.221 | 0.237 | 0.051 |
| 0.016 | 0.132 | 0.184 | 0.179 | 0.165 | 0.029 |
| Diluent | 0.067 | 0.093 | 0.109 | 0.090 | 0.021 |

Table 7, below, contains the clinical data and test results for patients with ulcerative colitis that participated in the study. Table 8, below, contains the clinical data and test results for patients with Crohn's disease that participated in the study. Table 9, below, contains the clinical data and test results for patients with irritable bowel syndrome that participated in the study. Table 10, below, contains the clinical data and test results for health patients that participated in the study.

TABLE 7

Clinical data and ELISA results for ulcerative colitis patients.

| Patient ID | Sex | Age Range | Disease | Disease Activity | ELISA OD$_{450}$ | ELISA Result |
|---|---|---|---|---|---|---|
| UC1 | F | 10-19 | UC | INACTIVE | 0.053 | NEGATIVE |
| UC2 | F | 5-9 | UC | INACTIVE | 0.107 | NEGATIVE |
| UC3 | F | 5-9 | UC | ACTIVE | 0.058 | NEGATIVE |
| UC4 | M | 10-19 | UC | INACTIVE | 0.048 | NEGATIVE |
| UC5 | M | 10-19 | UC | ACTIVE | 0.512 | POSITIVE |
| UC6 | F | 10-19 | UC | ACTIVE | 0.061 | NEGATIVE |
| UC7 | M | 5-9 | UC | ACTIVE | 0.211 | POSITIVE |
| UC8 | M | 10-19 | UC | ACTIVE | 0.106 | NEGATIVE |
| UC9 | M | 10-19 | UC | INACTIVE | 0.804 | POSITIVE |
| UC10 | M | 10-19 | UC | ACTIVE | 0.091 | NEGATIVE |
| UC11 | F | 10-19 | UC | ACTIVE | 0.169 | POSITIVE |
| UC12 | F | 10-19 | UC | ACTIVE | 0.209 | POSITIVE |
| UC13 | F | 10-19 | UC | ACTIVE | 0.351 | POSITIVE |
| UC14 | F | 10-19 | UC | ACTIVE | 0.198 | POSITIVE |
| UC15 | F | 5-9 | UC | ACTIVE | 0.098 | NEGATIVE |
| UC16 | F | 5-9 | UC | ACTIVE | 0.050 | NEGATIVE |
| UC17 | F | 10-19 | UC | ACTIVE | 0.091 | NEGATIVE |
| UC18 | M | 10-19 | UC | ACTIVE | 0.603 | POSITIVE |
| UC19 | M | 10-19 | UC | ACTIVE | 0.091 | NEGATIVE |
| UC20 | F | 10-19 | UC | ACTIVE | 0.142 | POSITIVE |
| UC21 | M | 10-19 | UC | ACTIVE | 0.074 | NEGATIVE |
| UC22 | F | 10-19 | UC | ACTIVE | 0.105 | NEGATIVE |
| UC23 | M | 10-19 | UC | INACTIVE | 0.256 | POSITIVE |
| UC24 | F | 0-4 | UC | ACTIVE | 0.308 | POSITIVE |
| UC25 | F | 5-9 | UC | ACTIVE | 0.072 | NEGATIVE |
| UC26 | M | 10-19 | UC | INACTIVE | 0.237 | POSITIVE |
| UC27 | M | 10-19 | UC | ACTIVE | 0.048 | NEGATIVE |
| UC28 | M | 10-19 | UC | ACTIVE | 0.049 | NEGATIVE |
| UC29 | M | 10-19 | UC | ACTIVE | 0.059 | NEGATIVE |
| UC30 | F | 10-19 | UC | INACTIVE | 0.047 | NEGATIVE |
| UC31 | M | 10-19 | UC | ACTIVE | 0.055 | NEGATIVE |
| UC32 | M | 10-19 | UC | INACTIVE | 0.044 | NEGATIVE |
| UC33 | F | 10-19 | UC | ACTIVE | 0.043 | NEGATIVE |
| UC34 | M | 5-9 | UC | ACTIVE | 0.046 | NEGATIVE |
| UC35 | M | 10-18 | UC | INACTIVE | 0.043 | NEGATIVE |
| UC36 | M | 10-17 | UC | INACTIVE | 0.040 | NEGATIVE |
| UC37 | F | 10-19 | UC | ACTIVE | 0.047 | NEGATIVE |
| UC38 | F | 0-4 | UC | ACTIVE | 0.049 | NEGATIVE |
| UC39 | F | 5-9 | UC | INACTIVE | 0.363 | POSITIVE |
| UC40 | F | 10-19 | UC | INACTIVE | 0.046 | NEGATIVE |
| UC41 | M | 10-19 | UC | ACTIVE | 0.118 | NEGATIVE |
| UC42 | F | 50-59 | UC | ACTIVE | 0.230 | POSITIVE |
| UC43 | M | 10-19 | UC | ACTIVE | 0.051 | NEGATIVE |
| UC44 | F | 30-39 | UC | ACTIVE | 0.060 | NEGATIVE |
| UC45 | F | 50-59 | UC | ACTIVE | 0.465 | POSITIVE |
| UC46 | M | 50-59 | UC | ACTIVE | 0.274 | POSITIVE |
| UC47 | F | 30-39 | UC | ACTIVE | 0.141 | POSITIVE |
| UC48 | M | 60-69 | UC | ACTIVE | 0.184 | POSITIVE |
| UC49 | F | 40-49 | UC | ACTIVE | 0.397 | POSITIVE |
| UC50 | F | 40-49 | UC | ACTIVE | 0.337 | POSITIVE |
| UC51 | M | 30-39 | UC | ACTIVE | 0.143 | POSITIVE |

TABLE 8

Clinical data and ELISA results for Crohn's disease patients.

| Patient ID | Sex | Age Range | Disease | Disease Activity | ELISA OD$_{450}$ | ELISA Result |
|---|---|---|---|---|---|---|
| CD1 | M | 10-19 | CD | ACTIVE | 0.050 | NEGATIVE |
| CD2 | M | 10-19 | CD | ACTIVE | 0.113 | NEGATIVE |
| CD3 | M | 10-19 | CD | ACTIVE | 0.050 | NEGATIVE |
| CD4 | F | 10-19 | CD | ACTIVE | 0.381 | POSITIVE |
| CD5 | F | 10-19 | CD | ACTIVE | 0.058 | NEGATIVE |
| CD6 | M | 10-19 | CD | INACTIVE | 0.068 | NEGATIVE |
| CD7 | M | 10-19 | CD | ACTIVE | 0.066 | NEGATIVE |
| CD8 | M | 5-9 | CD | ACTIVE | 0.059 | NEGATIVE |
| CD9 | F | 10-19 | CD | ACTIVE | 0.059 | NEGATIVE |
| CD10 | F | 10-19 | CD | ACTIVE | 0.065 | NEGATIVE |
| CD11 | F | 10-19 | CD | INACTIVE | 0.055 | NEGATIVE |
| CD12 | M | 10-19 | CD | INACTIVE | 0.071 | NEGATIVE |
| CD13 | F | 10-19 | CD | ACTIVE | 0.065 | NEGATIVE |
| CD14 | M | 10-19 | CD | ACTIVE | 0.098 | NEGATIVE |
| CD15 | F | 10-19 | CD | ACTIVE | 0.099 | NEGATIVE |
| CD16 | M | 10-19 | CD | ACTIVE | 0.166 | POSITIVE |
| CD17 | F | 10-19 | CD | ACTIVE | 0.147 | POSITIVE |
| CD18 | M | 10-19 | CD | ACTIVE | 0.057 | NEGATIVE |
| CD19 | F | 10-19 | CD | ACTIVE | 0.084 | NEGATIVE |
| CD20 | M | 10-19 | CD | ACTIVE | 0.053 | NEGATIVE |
| CD21 | F | 10-19 | CD | ACTIVE | 0.074 | NEGATIVE |
| CD22 | M | 10-19 | CD | ACTIVE | 0.054 | NEGATIVE |
| CD23 | M | 0-5 | CD | ACTIVE | 0.055 | NEGATIVE |
| CD24 | M | 10-19 | CD | ACTIVE | 0.067 | NEGATIVE |
| CD25 | M | 10-19 | CD | ACTIVE | 0.099 | NEGATIVE |

TABLE 8-continued

Clinical data and ELISA results for Crohn's disease patients.

| Patient ID | Sex | Age Range | Disease | Disease Activity | ELISA OD$_{450}$ | ELISA Result |
|---|---|---|---|---|---|---|
| CD26 | M | 5-9 | CD | ACTIVE | 0.086 | NEGATIVE |
| CD27 | F | 10-19 | CD | ACTIVE | 0.043 | NEGATIVE |
| CD28 | F | 10-19 | CD | ACTIVE | 0.064 | NEGATIVE |
| CD29 | M | 5-9 | CD | INACTIVE | 0.039 | NEGATIVE |
| CD30 | M | 10-19 | CD | ACTIVE | 0.071 | NEGATIVE |
| CD31 | F | 10-15 | CD | ACTIVE | 0.109 | NEGATIVE |
| CD32 | M | 10-19 | CD | INACTIVE | 0.057 | NEGATIVE |
| CD33 | M | 10-19 | CD | ACTIVE | 0.141 | POSITIVE |
| CD34 | M | 10-19 | CD | INACTIVE | 0.045 | NEGATIVE |
| CD35 | F | 10-19 | CD | ACTIVE | 0.051 | NEGATIVE |
| CD36 | F | 10-19 | CD | ACTIVE | 0.132 | NEGATIVE |
| CD37 | F | 10-19 | CD | INACTIVE | 0.046 | NEGATIVE |
| CD38 | M | 10-19 | CD | ACTIVE | 0.057 | NEGATIVE |
| CD39 | F | 20-29 | CD | INACTIVE | 0.051 | NEGATIVE |
| CD40 | F | 20-29 | CD | ACTIVE | 0.053 | NEGATIVE |
| CD41 | M | 50-59 | CD | ACTIVE | 0.060 | NEGATIVE |
| CD42 | F | 50-59 | CD | ACTIVE | 0.062 | NEGATIVE |
| CD43 | M | 20-29 | CD | ACTIVE | 0.056 | NEGATIVE |
| CD44 | F | 60-69 | CD | ACTIVE | 0.130 | NEGATIVE |
| CD45 | M | 60-69 | CD | ACTIVE | 0.078 | NEGATIVE |
| CD46 | F | 40-49 | CD | ACTIVE | 0.116 | NEGATIVE |
| CD47 | M | 60-69 | CD | ACTIVE | 0.057 | NEGATIVE |

TABLE 9

Clinical data and ELISA results for Irritable bowel syndrome patients.

| Patient ID | Sex | Age Range | Disease | ELISA OD$_{450}$ | ELISA Results |
|---|---|---|---|---|---|
| IBS1 | F | 10-19 | IBS | 0.056 | NEGATIVE |
| IBS2 | M | 10-19 | IBS | 0.047 | NEGATIVE |
| IBS3 | M | 5-9 | IBS | 0.099 | NEGATIVE |
| IBS4 | M | 10-19 | IBS | 0.068 | NEGATIVE |
| IBS5 | M | 10-19 | IBS | 0.092 | NEGATIVE |
| IBS6 | F | 20-29 | IBS | 0.121 | NEGATIVE |
| IBS7 | F | 30-39 | IBS | 0.064 | NEGATIVE |

TABLE 10

Clinical data and ELISA results for healthy persons.

| Subject ID | Sex | Age Range | ELISA OD$_{450}$ | ELISA Results |
|---|---|---|---|---|
| D1 | F | 40-49 | 0.087 | NEGATIVE |
| D2 | M | 20-29 | 0.078 | NEGATIVE |
| D5 | M | 20-29 | 0.178 | POSITIVE |
| D15 | M | 50-59 | 0.041 | NEGATIVE |
| D17 | M | 50-59 | 0.039 | NEGATIVE |
| D18 | F | 40-49 | 0.069 | NEGATIVE |
| D19 | F | 60-69 | 0.050 | NEGATIVE |
| D20 | M | 70-79 | 0.039 | NEGATIVE |
| D21 | F | 70-79 | 0.104 | NEGATIVE |
| D22 | M | 60-69 | 0.045 | NEGATIVE |
| D24 | F | 50-59 | 0.054 | NEGATIVE |

In summary, the present invention is directed to non-invasive methods for aiding in the differentiation of ulcerative colitis from Crohn's disease by determining the presence of ANCA as a marker of ulcerative colitis. The present invention is further drawn to immunoassays, e.g., qualitative enzyme-linked immunoassays, that utilize antibodies specific to human immunoglobulins for the measurement of total endogenous ANCA in human feces. The present invention has been described in relation to particular embodiments which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects hereinabove set forth together with other advantages which are obvious and which are inherent to the method.

It will be understood that certain features and subcombinations are of utility and may be employed without reference to other features and subcombinations. This is contemplated by and is within the scope of the claims.

Having thus described the invention, what is claimed is:

1. A method for diagnosing ulcerative colitis by testing a fecal sample for an elevated level of anti-neutrophil cytoplasmic antibodies, the method comprising:
    obtaining a fecal sample from a person presenting with inflammatory bowel disease;
    determining whether there is an elevated level of anti-neutrophil cytoplasmic antibodies in the sample compared to an anti-neutrophil cytoplasmic antibody level in a healthy sample, wherein an elevated level of anti-neutrophil cytoplasmic antibodies is indicative of ulcerative colitis; and
    diagnosing the person with anti-neutrophil cytoplasmic antibodies present in the fecal sample with ulcerative colitis.

2. The method as recited in claim 1, further comprising:
    diluting the fecal sample.

3. The method as recited in claim 2, further comprising:
    contacting the fecal sample with neutrophil cytoplasmic antigens to create a treated sample.

4. The method as recited in claim 3, further comprising:
    contacting the treated sample with polyvalent antibodies to human immunoglobulin to create a readable sample.

5. The method as recited in claim 4, further comprising:
    determining an optical density of the readable sample at 450 nm, wherein the optical density corresponds to a level of anti-neutrophil cytoplasmic antibodies in the sample.

6. A diagnostic assay for diagnosing ulcerative colitis by determining whether a fecal sample contains an elevated level of anti-neutrophil cytoplasmic antibodies, the assay comprising:
    obtaining a human fecal sample from a person presenting with inflammatory bowel disease;
    diluting the fecal sample;
    contacting the diluted sample with neutrophil cytoplasmic antigens to create a treated sample;
    contacting the treated sample with polyvalent antibodies to human immunoglobulin to create a readable sample;
    determining the optical density of the readable sample at 450 nm; and
    determining whether the optical density indicates an elevated level of anti-neutrophil cytoplasmic antibodies compared to an anti-neutrophil cytoplasmic antibody level in a healthy sample, where an elevated level of anti-neutrophil cytoplasmic antibodies is an indicator of ulcerative colitis.

7. The diagnostic assay as recited in claim 6, wherein the anti-neutrophil cytoplasmic antibodies are one of IgG, IgE, IgM, IgD, IgA$_{sec}$, IgA, and combinations thereof.

8. The diagnostic assay as recited in claim 6, wherein the assay is selected from a group consisting of an enzyme-linked immunoassay and a lateral flow membrane test.

* * * * *

UNITED STATES PATENT AND TRADEMARK OFFICE
CERTIFICATE OF CORRECTION

| | | |
|---|---|---|
| PATENT NO. | : 7,736,858 B2 | Page 1 of 1 |
| APPLICATION NO. | : 10/656034 | |
| DATED | : June 15, 2010 | |
| INVENTOR(S) | : James Hunter Boone, David Maxwell Lyerly and Tracy Dale Wilkins | |

It is certified that error appears in the above-identified patent and that said Letters Patent is hereby corrected as shown below:

The title was incorrectly transcribed by the Patent Office.

Title Page and

Column 1, line 4:

(54) Title: delete "ANIT" and replace with --ANTI--

Signed and Sealed this

Sixteenth Day of November, 2010

David J. Kappos
*Director of the United States Patent and Trademark Office*